United States Patent [19]

Hadeishi

[11] Patent Number: 4,815,848
[45] Date of Patent: Mar. 28, 1989

[54] DEVICE FOR THE INDIVIDUAL ADJUSTMENT OF THE INTENSITY OF SEVERAL SPECTRAL LAMPS

[75] Inventor: Tetsuo Hadeishi, Kensington, Calif.

[73] Assignee: Gruen-Optik Wetzlar GmbH, Wetzlar, Fed. Rep. of Germany

[21] Appl. No.: 946,048

[22] PCT Filed: Mar. 29, 1986

[86] PCT No.: PCT/DE86/00136
§ 371 Date: Nov. 28, 1986
§ 102(e) Date: Nov. 28, 1986

[87] PCT Pub. No.: WO86/05941
PCT Pub. Date: Oct. 9, 1986

[30] Foreign Application Priority Data

Mar. 28, 1985 [DE] Fed. Rep. of Germany ....... 3511255

[51] Int. Cl.⁴ ............................ G01J 3/42; G01J 3/28
[52] U.S. Cl. .................................... 356/320; 356/326
[58] Field of Search .............. 356/319, 320, 326, 312, 356/315, 328; 250/205, 231 R; 315/151, 152, 158

[56] References Cited

U.S. PATENT DOCUMENTS 3,586,441 6/1971 Smith et al. .................... 356/320
4,281,245 7/1981 Brogardh et al. ............. 250/205 X
4,449,821 5/1984 Lee .................................... 356/319

OTHER PUBLICATIONS

Mitchell, Gordon L., "Optical Measurements with the Lights On", Laser Focus, Mar. 1981, pp. 70–74.
Laser Focus, vol. 17, No. 3, Mar. 1981, N.Y., G. L. Mitchell.

Primary Examiner—Eugene R. LaRoche
Assistant Examiner—Nathan W. McCutcheon
Attorney, Agent, or Firm—Foley & Lardner, Schwartz, Jeffery, Schwaab, Mack, Blumenthal & Evans

[57] ABSTRACT

A device for the individual adjustment of the intensity of several spectral lamps (1, 2), the radiation of which is combined into a common ray path (4), is distinguished by the fact that a device is provided for the modulation of the emission of each of the spectral lamps (1,2) with a different frequency, a beam-splitting mirror (8) for extraction of a part of the total radiation is inserted into the common ray path (4), a photoelectric receiver (9) is provided for the generation of an electrical signal which is proportional to the intensity of the extracted radiation, and frequency filters (11, 23) which are tuned to the modulation frequencies of the spectral lamps (1, 2) are arranged behind the photoelectric receiver (9), regulators, comprising a phase-locked loop (PLL) (12, 22), an automatic gain control (AGC) (13, 23) and a power amplifier (10, 20), for control of the intensity of the respective spectral lamp (1, 2) being allocated to the frequency filters.

6 Claims, 2 Drawing Sheets

DEVICE FOR THE INDIVIDUAL ADJUSTMENT OF THE INTENSITY OF SEVERAL SPECTRAL LAMPS

BACKGROUND OF THE INVENTION

The invention relates to a device according to for the individual adjustment of the intensity of several spectral lamps.

Absorption spectrometers, in particular, frequently contain several spectral lamps for the generation of measuring radiation which is suitable for the sample to be investigated in each case. When the lamps are activated individually in sequence, their respective operating parameters can be regulated, in a simple fashion, directly by means of the central power unit, as a function of a measurable variable derived from the measuring ray path. However, if all the lamps are activated simultaneously and combined into a common measuring ray bundle with the aid of reflecting mirrors, several regulators, arranged after the common power unit, are required for individual adjustment of the operating parameters of the individual lamps. Individual control of these regulators as a function of a signal derived from the measuring ray bundle is not possible, since the parts of the radiation belonging to the individual lamps in the common measuring ray bundle cannot be separated. Stabilization of fluctuating emission intensities of individual lamps or, e.g., controlled matching of the radiation composition to various samples is thus not possible.

SUMMARY OF THE INVENTION

The invention therefore has the object of specifying a device with which the intensity of several spectral lamps, operated parallel to one another, can be matched, in a simple fashion, to the various requirements as a function of a regulation variable derived from the total measuring ray bundle.

BRIEF DESCRIPTION OF THE DRAWINGS

Exemplary embodiments of the invention are represented schematically in the drawing and are described below. In detail.

DESCRIPTION OF THE PREFERRED EMBODIMENT

Figure 1:
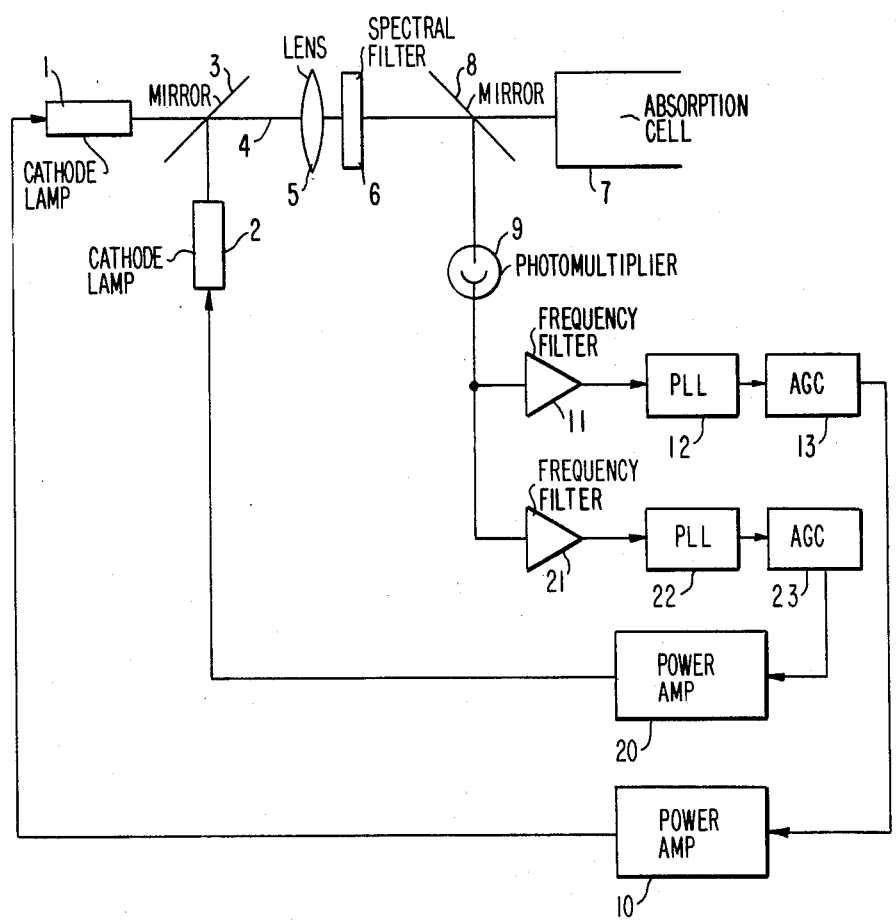
FIG. 1 shows a device having several control loops connected in parallel.

In FIG. 1, radiation from two different hollowcathode lamps 1, 2, e.g. for the elements Se and Hg, are combined into a common ray path 4 with the aid of a beam-splitting mirror 3. A lens 5 collects the radiation and passes it through an optionally engageable spectral filter 6 into an absorption cell 7. A semi-transparent mirror 8, which reflects part of the total radiation towards a photomultiplier 9, is inserted into the ray path in front of the absorption cell 7.

The operating voltage of the hollow-cathode lamp 1 is generated by a power amplifier 10 and modulated, e.g., with a frequency of 2 kHz. In the same manner, the hollow-cathode lamp 2 is supplied by the power amplifier 20, which modulates the emission of the lamp with 9 kHz, for example. By means of the modulation in each case, the components of the radiation in the measuring ray path belonging to both lamps receive an identifier, which is also contained in the electrical signal generated by the photomultiplier 9. Both components of the signal can be separated by frequency filters 11 and 21. Phase-locked loops (PLL) 12 and 22 and automatic gain controls (AGC) 13 and 23 ensure phase-locked control of the power amplifiers 10 and 20 in phase with their modulation frequencies.

Figure 2:
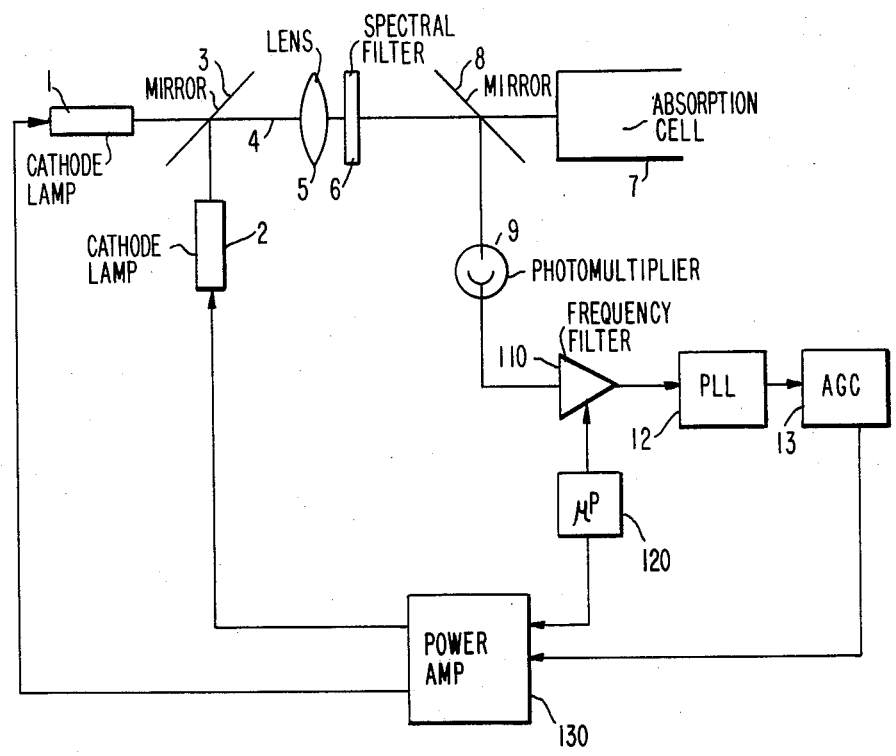
FIG. 2 shows a device having an alternately tuneable control loop.

In FIG. 2, the elements which correspond to FIG. 1 are provided with the same reference numbers as there. The frequency filter 110, arranged after the photomultiplier 9, is electronically tuneable in this case. It obtains the control signals for this from the circuit arrangement 120, e.g. a microprocessor.

The power amplifier 130 has two outputs having different frequency-modulated supply voltages for the lamps 1 and 2. The gain control signal coming from the regulator 13 is also fed, synchronously with the tuning of the frequency filter 110 by means of the circuit arrangement 120, to the correspondingly modulated output signal of the power amplifier 130. The supply voltage at the other output, or further outputs which may be present, of the power amplifier 130 remains unregulated during this time.

Taking into account the very fast switching times for the tuning of the frequency filter and for the transient oscillation of the gain control loop compared to the general fluctuations of the emission intensities of the lamps, this is acceptable. The advantage is in a further reduction of the expense of the electronic components. Of course, a control signal for the measurement switching circuit (not shown) arranged after the absorption cell 7 can be taken from the circuit arrangement 120. The signal evaluation can be further simplified by the use of digital frequency filters, known per se.

I claim:

1. A device for the individual adjustment of the intensity of a plurality of spectral lamps, the radiation of which is combined into a common ray path, comprising:
   (a) modulating means for the modulation of the emission of each of the spectral lamps with a different frequency,
   (b) beam-splitting mirror means for extraction of a part of the total radiation that is inserted into the common ray path,
   (c) photoelectric receiver means for the generation of an electrical signal which is proportional to an intensity of the extracted radiation,
   (d) first and second frequency filter means which are tuned to respective modulation frequencies of the spectral lamps and are connected to an output of the photoelectric receiver means, and
   (e) first and second regulator means, each comprising a phase-locked loop, an automatic gain control and a power amplifier, for control of the intensity of the respective spectral lamps and are connected to respective outputs of the first and second frequency filter means.

2. The device as claimed in claim 1, wherein said first and second frequency filter means are connected in parallel to one another, which amplifier circuits being connected to respective outputs of said first and second regulator means.

3. The device as claimed in claim 1, wherein digital frequency filters are provided.

4. The device as claimed in claim 2, wherein digital frequency filters are provided.

5. A device for the individual adjustment of the intensity of a plurality of spectral lamps, the radiation of which is combined into a common ray path comprising:
(a) modulating means for the modulation of emission from each of the spectral lamps with a different frequency,
(b) beam-splitting means for extraction of a part of the total radiation that is inserted into the common ray path,
(c) photoelectric receiver means for the generation of an electrical signal which is proportional to an intensity of the extracted radiation,
(d) electronically tunable frequency filter means which is tuned to respective modulation frequencies of the spectral lamps and connected to an output of said photoelectric receiver means,
(e) regulator means comprising a phase-locked loop, an automatic gain control, and a power amplifier having differently modulated outputs for operation of the spectral lamps, and
(f) circuitry means for alternating tuning of said frequency filter means to the modulation frequencies of the spectral lamps and switching of a signal of the automatic gain control to a correspondingly modulated output of the power amplifier.

6. The device as claimed in claim 5, wherein digital frequency filters are provided.

* * * * *